US007878044B2

(12) United States Patent
Andle

(10) Patent No.: US 7,878,044 B2
(45) Date of Patent: Feb. 1, 2011

(54) SENSOR, SYSTEM, AND METHOD, FOR MEASURING FLUID PROPERTIES USING MULTI-MODE QUASI-SHEAR-HORIZONTAL RESONATOR

(75) Inventor: Jeffrey C. Andle, Falmouth, ME (US)

(73) Assignee: Delaware Capital Formation, Inc., Wilmington, DE (US)

( * ) Notice: Subject to any disclaimer, the term of this patent is extended or adjusted under 35 U.S.C. 154(b) by 337 days.

(21) Appl. No.: 12/036,125

(22) Filed: Feb. 22, 2008

(65) Prior Publication Data

US 2009/0216467 A1    Aug. 27, 2009

(51) Int. Cl.
*G01N 29/02* (2006.01)
*G01N 29/46* (2006.01)
(52) U.S. Cl. .................. 73/24.06; 73/31.06; 73/32 A; 73/54.41; 73/61.49; 73/61.75; 73/64.53
(58) Field of Classification Search ............ 73/579, 73/19.03, 24.01, 24.06, 31.06, 32 A, 54.23–54.26, 73/53.26, 54.41, 61.49, 61.75, 64.42, 64.53
See application file for complete search history.

(56) References Cited

U.S. PATENT DOCUMENTS

| | | | |
|---|---|---|---|
| 5,532,538 A | 7/1996 | Jin et al. | |
| 5,708,191 A | 1/1998 | Greenwood et al. | |
| 5,741,961 A | 4/1998 | Martin et al. | |

(Continued)

FOREIGN PATENT DOCUMENTS

DE    102006 003649 A1    8/2007

(Continued)

OTHER PUBLICATIONS

"Two-Dimensional closed form analysis of TSM Quartz Resonators", T. Lindenbauer and B. Jakoby, Vienna University of Technology, Institute of Sensor and Actuator Systems. Presented Eurosensor XIX, Barcelona, Spain, Sep. 2005. Downloaded from http://www.samlab.unine.ch/ConferenceCD/EuroSensorsXIX/pdfs/TB14.pdf.

(Continued)

*Primary Examiner*—Hezron Williams
*Assistant Examiner*—Rose M Miller
(74) *Attorney, Agent, or Firm*—Shalom Wertsberger; Saltamar Innovations

(57) ABSTRACT

A system and a method for providing information on two of the three variables, density ($\rho$), viscosity ($\eta$), and elastic modulus (c) of a fluid, such that independent knowledge of one variable allows the remaining two variables to be measured by a single sensor. The present invention relies on the interaction of a predominantly shear horizontal acoustic wave device ("quasi-shear-horizontal") with the fluid, so as to measure subtle differences in the interaction of two or more acoustic resonance states or waveguide modes of a multi-mode resonator or waveguide, and to derive the desired fluid characteristics therefrom. The most preferred embodiment is a dual-mode coupled resonator filter geometry with one resonant mode having a high degree of symmetry and the other having a high degree of anti-symmetry. By combining the additional information of multi-moded operation with the inherent ability of a horizontally-polarized quasi-shear-horizontal acoustic wave device (AWD) to operate in fluid environments, one obtains a multi-mode quasi-shear-horizontal (MMQSH) resonator.

19 Claims, 8 Drawing Sheets

U.S. PATENT DOCUMENTS

| | | |
|---|---|---|
| 5,793,146 A | 8/1998 | Wright |
| 5,798,452 A | 8/1998 | Martin et al. |
| 5,886,250 A | 3/1999 | Greenwood |
| 6,082,180 A | 7/2000 | Greenwood |
| 6,082,181 A | 7/2000 | Greenwood |
| 6,543,274 B1 | 4/2003 | Herrmann et al. |
| 7,002,281 B2 | 2/2006 | Andle |
| 7,007,546 B2 | 3/2006 | Andle |
| 7,181,957 B2 | 2/2007 | Andle |
| 7,219,537 B2 | 5/2007 | Andle |
| 7,267,009 B2 * | 9/2007 | Liu et al. .................. 73/649 |
| 7,287,431 B2 * | 10/2007 | Liu et al. .................. 73/649 |
| 7,383,731 B2 * | 6/2008 | Liu et al. .................. 73/602 |
| 2007/0144240 A1 | 6/2007 | Andle |

FOREIGN PATENT DOCUMENTS

| | | |
|---|---|---|
| EP | 0542 269 A1 | 5/1993 |
| WO | WO2005114138 A2 | 12/2005 |

OTHER PUBLICATIONS

Search report issued by the European Patent Office in EP09152744.0, a corresponding European application to the curent application.

\* cited by examiner

SENSOR, SYSTEM, AND METHOD, FOR MEASURING FLUID PROPERTIES USING MULTI-MODE QUASI-SHEAR-HORIZONTAL RESONATOR

FIELD OF THE INVENTION

The present invention relates generally to sensors, and more particularly to sensors for viscosity, elastic modulus, and density of fluids.

BACKGROUND OF THE INVENTION

The measurement of fluid properties is important in many industrial and consumer machines and processes. While applicable to many fields, the measurement of fluid properties is of significant concern for lubrication and power transfer equipment, which is based on mineral oils and related synthetic compounds. Loss of functionality of these fluids results in premature aging of the associated equipment and, sometimes, in catastrophic failure.

Presently, the characterization of such fluids is primarily accomplished using laboratory analysis of fluid samples. There is a growing desire to place sensors for continuous monitoring directly into the equipment.

In U.S. Pat. Nos. 5,708,191, 5,886,250, 6,082,180 and 6,082,181, Greenwood et al. present a family of densitometer sensor designs that employ input and output transducers to measure changes in reflected signal strength of acoustic waves as they reflect near a critical angle of incidence. These viscometers measure either viscosity-density product or elasticity-density product based on the reflection of acoustic waves from the liquid-loaded face of a solid material supporting the transducers. The sensors measure reflection coefficients of the wave from solid-liquid boundaries upon a few reflection events of a pulsed or continuous-wave signal. Such methods offer less sensitivity and resolution of the measured quantity than do resonant, multi-reflective, or surface generated acoustic wave devices. The latter enjoy higher sensitivity from the continuous interaction of their acoustic waves with the solid-liquid interface. The discrete-reflection methods do not enjoy the simplicity of manufacture or operation of a continuous acoustic wave interaction surface, nor do they provide similar sensitivity or resolution. The discrete reflection methods assume a fixed elastic modulus (for the more common compressional wave version) or viscosity (for the less common shear wave version) in order to extract density information from the measured response of the sensor.

Measuring the density-viscosity product is done by immersing a resonator manufactured on a piezoelectric substrate and supporting a transverse shear mode of resonance, typically a disc of quartz crystal of AT cut or langasite of approximately Y-cut, into the liquid and measuring the shift in resonant frequency or the loss of power at resonance. Further known is the use of two-port devices based on multi-pole resonators using shear wave acoustic modes, such as the SH-SAW (Shear Horizontal—Surface Acoustical Wave), SHAPM (Shear Horizontal Acoustical Plate Mode), MPS (Monolithic Piezoelectric Sensor) e.g. as described in U.S. Pat. No. 6,033,852, issued Mar. 7, 2000 to Andle et al.

U.S. Pat. No. 5,741,961 and U.S. Pat. No. 5,798,452 to Martin et al. disclosed a method in which two acoustic wave sensors having different surface treatment exhibit essentially identical responses to viscosity-density product but differing responses to the density. A reference sensor provides data on the product of viscosity and density and employs a smooth surface. The second sensor has an intentionally roughened surface, typically having grooves or pits in its surface for trapping a certain volume of fluid. The added mass creates a finite frequency shift with little or no power loss in addition to the power loss and frequency shift of the viscously entrained liquid. The density-viscosity product is available via the common-mode frequency shift. While this method is attractive, it incurs difficulties in sensor-to-sensor reproducibility, particularly when the two sensors are manufactured on different substrates.

The addition of such grooves to one of a pair of shear horizontal surface acoustic wave (SH-SAW, also known as Love Wave, surface transverse wave, and the like) sensors is also disclosed (Herrmann et al., U.S. Pat. No. 6,543,274), and the extension of this approach to SHAPM sensors is contemplated herein. This method offers higher frequency, smaller size, and improved sensitivity at the expense of manufacturing complexity and available dynamic range. However Herrmann still finds the use of two completely separate but identical (other than the corrugations) sensor elements necessary for measuring both parameters, and therefore it does not overcome the sensor-to-sensor limitations of the Martin device. It also incurs less accurate viscosity measurement due to the higher operating frequency, which exacerbates shear thinning and Maxwellian viscoelastic issues that are known in the field of rheology.

In a U.S. Pat. No. 7,007,546, issued Mar. 7, 2006 titled "Measurement, Compensation and Control of Equivalent Shear Rate in Acoustic Wave Sensors" (which is incorporated herein by reference in its entirety), the inventor of the present application disclosed a method for measuring viscosity and shear rate at which the measurement is performed by utilizing an acoustic wave sensor, and calculating the shear rate as a function of the characteristic rate of fluid movement in response to a given power transmitted to a fluid, and the viscosity of the fluid. The acoustic wave device has a characteristic relationship between input power, output power, and an acoustic wave amplitude at a selected region between the input and output transducer. The acoustic wave device is coupled to the measured fluid. A predetermined power level $P_{in}$ of a harmonic signal is applied to an input transducer, to impart an acoustic wave at the selected region. Output power level $P_{out}$ is measured at the output transducer. Using the characteristic relationship, and the input and output power levels, the amplitude of the average acoustic wave imparted to the fluid is calculated. Measuring the viscosity of the fluid to obtain a measured viscosity at the selected region, allows the calculation of the shear rate of the fluid at the selected region, by using the frequency, the viscosity measurement, and the acoustic wave amplitude. This invention may be beneficially used with the present invention as explained below.

In U.S. patent application Ser. No. 10/597,487 filed Feb. 14, 2007 and published as US -2007-0144240-A1, the applicant described a two-port, two-pole coupled resonator with a textured entrapment layer in contact with a fluid to be measured, such as a liquid or a gas, which allows measurement of viscosity and density of the fluid. However, the manufacture of a textured entrapment layer adds complexity to such a device. Nonetheless, the structures and methods disclosed in the 10/597,487 application may be practiced in conjunction with the present invention. It is noted that the incorporation of a textured surface is not necessary to embody aspects of the present invention.

There is therefore a clear advantage for sensors and measurement methods that will allow measurement of as many parameters of a fluid as possible, integrated into a single device. While such devices were contemplated, they suffer from different disadvantages such as manufacturing complexity, unpredictability, low accuracy and the like. It is a goal of the present invention to provide a sensor capable of deducing at least two of the three parameters—viscosity, density, and elastic modulus, when the third parameter is known or assumed. It is a further goal of the present invention to provide a system and method that will perform such measurements using the sensor.

SUMMARY OF THE INVENTION

The present invention relies on the interaction of a predominantly shear horizontal acoustic wave device ("quasi-shear-horizontal") with the fluid, as is well known in the art for the measurement of viscosity. More specifically the invention relies on the subtle differences in the interaction of two or more acoustic resonance states or waveguide modes of a multi-mode resonator or waveguide. The most preferred embodiment is a dual-mode coupled resonator filter geometry with one resonant mode having a high degree of symmetry and the other having a high degree of anti-symmetry. By combining the additional information of multi-moded operation with the inherent ability of a horizontally-polarized quasi-shear-horizontal acoustic wave device (AWD) to operate in fluid environments, one obtains a multi-mode quasi-shear-horizontal (MMQSH) resonator.

The present invention seeks to provide information on two of the three variables, density ($\rho$), viscosity ($\eta$), and elastic modulus (c), such that independent knowledge of one variable allows the remaining two variables to be measured by a single sensor.

Thus there is provided a method of measuring at least two fluid properties selected from density, viscosity, and elastic modulus, when the third of said fluid properties is known or assumed, the method comprising the steps of:

providing a Multi Mode Quasi Shear Horizontal Resonator (MMQSHR) having an energy input, and a measuring surface for contacting said fluid, said measuring surface having at least a first region and a second region, and a separation area defined therebetween;

feeding said MMQSHR with excitation energy via said input, at a first and a second frequencies selected to excite a first and a second acoustic modes respectively, each of said acoustic modes causing a component of horizontal shear wave motion in said surface, wherein excitation in said first frequency further causing said regions to move in phase relative to each other;

and wherein excitation in said second frequency causes said two regions to move out-of-phase relative to each other, inducing a vertical displacement in said separation area;

measuring energy related parameters at said first mode and second mode;

calculating two of said fluid properties utilizing said energy related parameters and information relating to said third fluid property.

The regions need not be physically delineated in the device structure but rather may be defined by the acoustic energy profile of the device in each mode.

The energy related parameters may be selected for example from insertion loss, frequency shift, phase shift, amplitude, current change, equivalent series resistance, any combination thereof, and the like. In the preferred embodiment, MMQSHR comprises a piezoelectric crystal, and the input comprises an input transducer. The most preferred embodiment further comprises an output transducer, and a ground electrode to which the input and output transducers are referenced. However non-piezoelectric materials and other methods of imparting energy to the MMQSHR are also contemplated. It is noted that the MMQSHR may employ any convenient structure, such as, by way of example, of bulk acoustic wave resonator, planar resonator, and shear horizontal surface acoustic wave resonator.

In certain embodiments, the measuring surface may be corrugated, and the method further comprising the step of calculating said fluid density responsive to changes in energy related parameters due to fluid trapped in said corrugations.

There is further provided a system for measuring at least two fluid properties selected from density, viscosity, and elastic modulus, when the third of said fluid properties is known or assumed, the system comprising:

A Multi-Mode Quasi Shear Horizontal (MMQSHR) resonator having
   a measuring surface for contacting said fluid;
   an energy input port and an energy output port;
   at least a first region and a second region, and a separation area defined therebetween;

excitation circuitry coupled at least to said energy input, and constructed to impart two acoustic modes of resonant motion to said surface;

measurement circuitry constructed to measure at least one parameter of the energy inputted into the MMQSHR resonator or outputted therefrom;

wherein said two acoustic modes are selected to cause a component of horizontal motion with differing polarity relationships at various regions of the surface of said surface.

The system may be further equipped with an optical and/or mechanical monitor to monitor displacement of the separation area. The system may further comprise calculator or computer circuitry for calculating said fluid properties, utilizing information obtained from said measurement circuitry.

In the preferred embodiment the MMQSH comprises a piezoelectric monolithic crystal filter, but other structures such as a piezoelectric transverse coupled resonator filter, and electromagnetic acoustic transducers are also contemplated.

The present invention further contemplates providing excitation energy in combination of differing power levels at the at least two frequencies, so as to cause said surface to impart various shear rates to the fluid at each of said frequencies, allowing the measurements to be made at varying shear rate.

In yet another optional aspect of the invention there is provided a resonator comprising a region of added mass defining trapped energy region, said trapped energy region supporting a plurality of laterally confined modes, said modes interacting with at least one transducer, said transducer providing electrical impedance relating to energy loss in said trapped energy resonator.

SHORT DESCRIPTION OF DRAWINGS

The summary above and the following detailed description will be better understood in view of the enclosed drawings, which depict details of preferred embodiments. It should however be noted that the invention is not limited to the precise arrangement shown in the drawings and that the drawings are provided merely as examples.

DETAILED DESCRIPTION

In layman's terms, the preferred embodiment provides a piezoelectric plate having a surface that encloses an area in which acoustic wave energy is confined. The various multiple resonant modes of the acoustic resonator have vibrational motion with differing polarity relationships at various locations on said surface. The resonant modes are most preferably all derived from the lateral trapped energy anharmonics of a single thickness harmonic of a single acoustic wave type. In general there exist three bulk acoustic wave types and at least one surface wave type in any given device geometry. One of the bulk waves is a quasi-compressional wave and the other two are quasi-shear waves. The most preferable case is to use the quasi shear wave with the highest piezoelectric coupling possible and the highest degree of horizontal polarization possible. Nonetheless it is possible to practice the invention using the fundamental anharmonics of the two quasi-shear wave types at the at least two modes of resonance.

In the most preferred embodiment there are at least two adjacent regions in which a tangential (in-plane) movement with respect to the surface is induced. At a first resonant frequency the tangential movement in the two regions is in phase (0°) and vertical motion is induced primarily at the outer edges, i.e. the outlying areas, of the regions. At a second resonant frequency the tangential movement in the regions is out-of phase (180°), and the area between the regions experiences vertical motion of substantially higher amplitude than at the first resonant frequency. As explained below, utilizing combinations of these movement types allows measurement of any two of the three measured fluid characteristics—i.e. viscosity, elastic modulus, and density—when the third characteristic is known or assumed. The skilled in the art will recognize that excitation of the resonator at a frequency other than the natural resonant frequencies of the various supported modes will result in energy distributions with different phase relationships that will generate a superposition of the acoustic resonances at nearby frequencies having variations of the out-of-plane movement distribution. While such excitation at multiple frequencies will result in differing degrees of out of plane motion, the advantages of exciting at or near the natural resonant frequencies will be apparent to one skilled in the art.

In these specifications, the terms vertical motion and vertical displacement relate to out-of-plane motion or displacement, i.e. a motion that is normal to the plate active plane.

Figure 1:
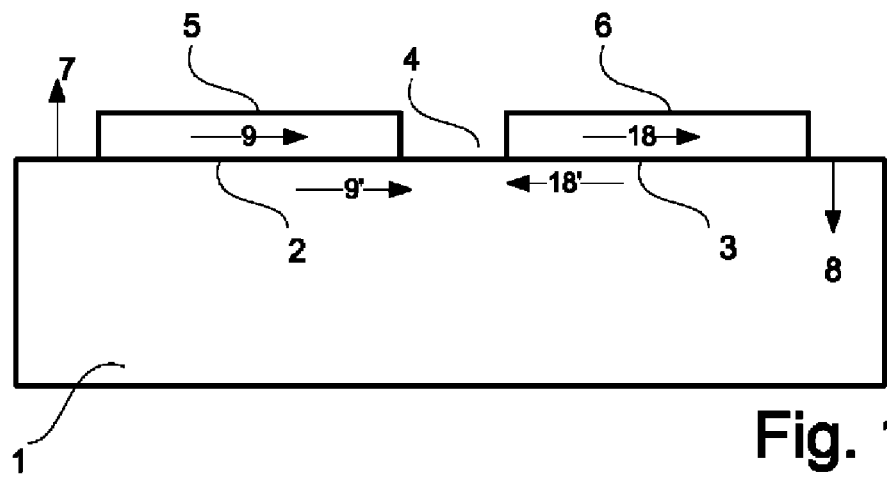
FIG. 1 depicts a basic embodiment of a sensor structure, depicting selected movement vectors under ideal conditions.

FIG. 1 represents a schematic section through a simplified sensor comprising piezoelectric plate 1 forming a coupled resonator by causing a shear horizontal movement in regions 2 and 3 relative to the plate face. Inducing such movement is well known in the art and by way of example, may be provided by transducer 5 and 6 respectively. FIG. 1 further depicts the plate movement at a given moment in time, where the regions 2 and 3 are moving in phase with each other, as shown by the horizontal arrows 9 and 18. It is noted that while the separating inter-region space 4 between the two regions experiences little if any vertical movement, the edges of the regions show a vertical movement depicted by arrows 7 and 8, as a result of a 'buckling' movement of the plate surface. However, when the plate regions 2 and 3 move in opposite phases as depicted by arrows 9' and 18', separating space 4 will experience significant vertical movement while the edges of the region will experience vertical movement in the opposite direction. As will become clear these two modes of vibration could also be excited by a single transducer of suitable design and the figure should not be construed as limiting.

A nearly purely horizontal shear wave excitation is the most preferable embodiment; however numerous "tilted" shear wave substrates with desirable properties are known. By way of non-limiting example, SC-cut quartz offers excellent vibration and acceleration insensitivity with tilted quasi-shear-horizontal modes. It is noted that SC-cut is commonly used to simultaneously excite two wave types with differing out of plane components in frequency control applications. The reader is reminded that these specifications concentrate on a purely horizontal polarization merely for illustrative purposes and to increase understanding of the invention, and that the invention encompasses the use of such substrates as will be recognized by the skilled in the art, to produce similar functionality.

Figure 2:
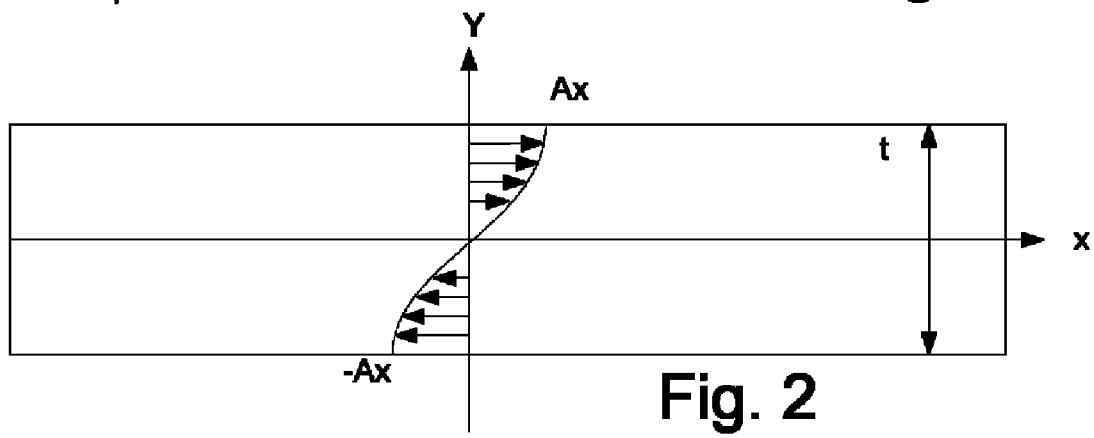
FIG. 2 depicts simplified wave propagation in a laterally unbounded plane.

The invention utilizes the well-known difference between an unbounded plane wave and a trapped energy wave having a finite beam width. A simplified example depicted schematically in FIG. 2, shows a simple plate of thickness, t, along Y with a wave displacement $U_X = A_X \sin(n\pi Y/t)$. The plate supports resonances at any odd integral multiple of n; however practical issues favor n=1, as depicted. Even values of n require a $\cos(n\pi Y/t)$ dependence but do not couple to thickness field excitation without the use of composite resonators as disclosed in applicants pending patent application U.S. Ser. No. 11/814,074. Thus, when examining an infinite plate of material with thickness, t, along the Y axis centered at Y=0 and consisting of a piezoelectric material such that an electric field along Y, $E_y$, leads to a shear XY stress in the bulk of the crystal. A resonance condition occurs that satisfies the stress-free boundary conditions by having acoustic displacements, $U_X(Y) = A_X \sin(n\pi Y/t)$. The wave has no bounds in X or Z and has pure shear displacement with tangential (horizontal) polarization with respect to a planar surface. The wave has a wave-vector, $K_y = n\pi/t$. The shear wave condition, that the scalar dot product of displacement and wave-vector, U·K, be zero, is satisfied. The device supports a family of nth order frequency harmonics of each of the three bulk wave types that are electrically coupled to the Y-directed electric field. For clarity of explanation it is assumed that this electric field only couples to a single quasi-shear-horizontal bulk wave and that a single series of harmonics exists.

Such an ideal resonator would have no interactions with an ideal, inviscid, fluid since there would exist no coupling between the pure shear mode of the substrate and the compressional waves that could exist in an ideal (inviscid) fluid. Allowing for Newtonian viscosity, η, and density, ρ, in the fluid, an energy transfer of the shear wave into the fluid would exist, where viscous effects would convert the energy from coherent acoustic vibrations into heat. However, in the case of an ideal resonator, there would be no radiation of compressional waves.

The ideal resonator, constrained in only one dimension, is not practical and real resonators have finite lateral dimensions. Introducing finite dimension, w, along Z introduces a lateral variation to $U_X(Y,Z)$ that can be simplistically estimated as either $U_X(Y,Z)=A_X \sin(n\pi Y/t)\cos(m\pi Z/w)$ or $A_X \sin(n\pi Y/t)\sin(m\pi Z/w)$ where the formula using cos( ) is associated with odd values of m, and the formula using sin( ) with even values of m.

Figure 3:
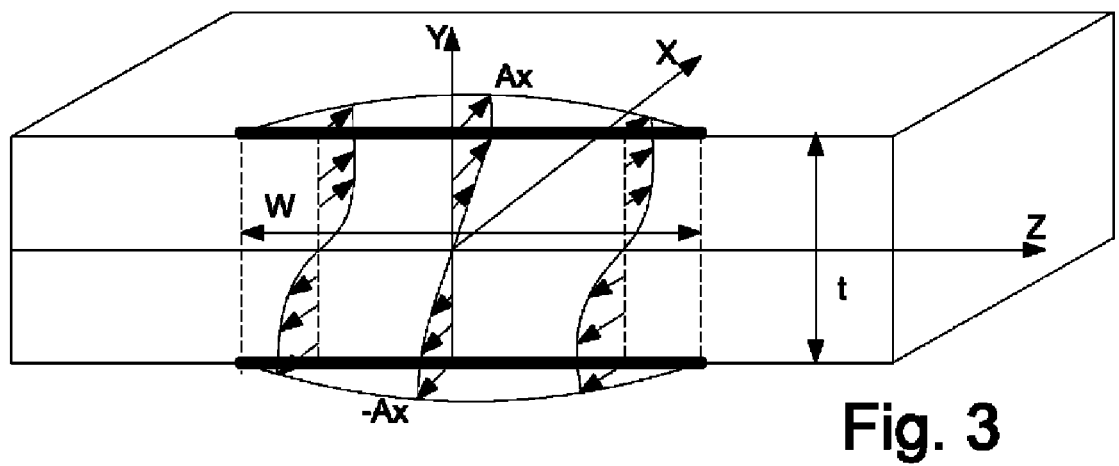
FIG. 3 depicts simplified wave propagation in a given width.

FIG. 3 depicts a simple plate of thickness t, along Y with energy trapping to a width, w, along Z and a wave displacement $U_X=A_X \sin(n\pi Y/t)\cos(m\pi Z/w)$. The plate supports resonances at any integral multiple of n and m; however practical issues favor n=1, as depicted. In practice the trapping is imperfect and fields leak beyond the electrode width, w. In such real resonators the value of m is slightly lower than each integer, M−δ. For clarity the electrodes are not shown as having length in the X dimension.

The wave-vector gains a Z component, $K_z=m\pi/w$; however, the shear wave condition of U·K=0 is still satisfied with a purely X polarized (pure shear horizontal) wave. The pure shear solution has tangential polarization at all points on a planar boundary.

Figure 4:
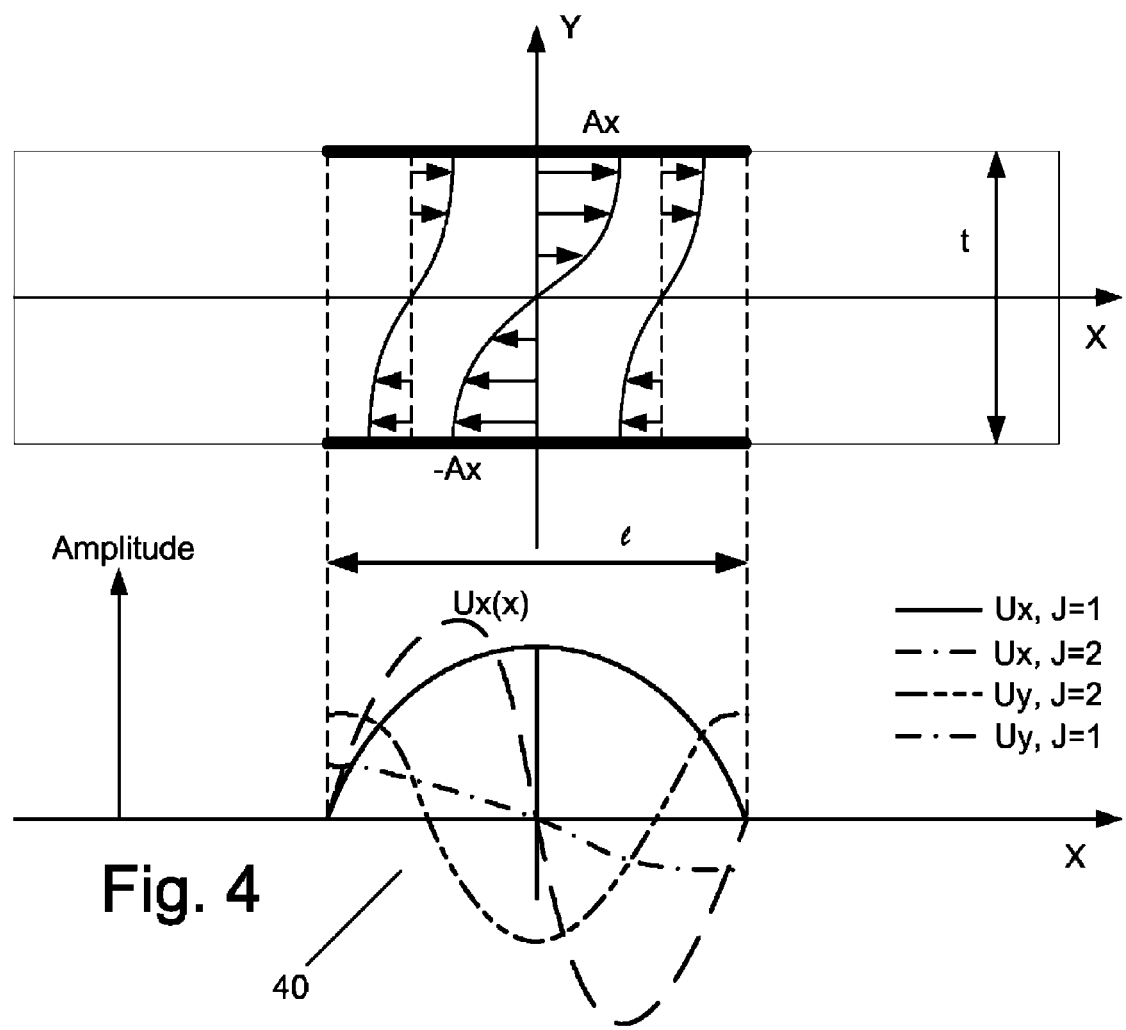
FIG. 4 depicts simplified wave propagation in several modes of excitation, depicting symmetric and anti-symmetric wave profiles.

FIG. 4 shows a simple plate of thickness, t, along Y and finite length, l, along X. Mode profiles 40 are shown with a wave displacement for n=1 and j=1 as $U_X=A_X \sin(\pi Y/t)\cos(\pi X/l)$ and for n=1 and j=2 as $U_X=A_X \sin(\pi Y/t)\sin(2\pi X/l)$. In practice there is a finite extension of the wave beyond the electrodes and j=J−δ. Also shown are the corresponding amplitude components, $U_Y(X,Y)=(t/l)A_X \sin(\pi X/l)\sin(\pi Y/t)$ for j=1 and $U_Y(X,Y)=(2t/l)A_X \cos(2\pi X/l)\sin(\pi Y/t)$ for j=2.

In a QCM based embodiment, at least two resonant frequencies corresponding to the same values of n and m, but having differing odd values of j, would be used to excite the QCM crystal. The power losses caused primarily due to viscosity would be nearly identical for at least those two resonant frequencies; however, the power losses associated with the vertical components of motion would differ in proportion to the squares of the values of j. Electrical efficiency considerations will favor n=1, m=1, and the values of j being 1 and 3 respectively for the two resonant frequency modes; however, there are advantages to using additional odd values of j to obtain redundant data for minimization of measurement error. Electrical coupling of the modes of higher j order are typically diminished by 1/j, limiting the number of modes that are of practical value.

It is noted that an ideal mode profile associated with j=2 has zero integrated amplitude over the electrode length and will have very weak coupling to a traditional QCM (Quartz Crystal Microbalance) electrode structure. The next mode, j=3, has non-zero coupling to a solid electrode and can be used to practice the invention in a QCM having a single transducer, as proposed above.

In a monolithic crystal filter (MCF) based embodiment, at least one surface has the electrode split into input and output electrodes referenced to an opposing ground electrode. In such a two-transducer device the resonances associated with j=1 and j=2 are coupled and form a multi-mode bandpass filter response. Coupled resonator structures such as this offer the preferred embodiment since they also offer a separate input and output port by which an electrical transfer function can be defined, simplifying instrumentation design for such a device.

Thus, to summarize, a small motion perpendicular to the plane occurs in all resonators of finite dimension, as marked in FIG. 1 by arrows 7 and 8, which can be estimated as proportional to the in-plane motion 9 and 10, multiplied by a constant k, where k is proportional to the thickness to length (t/l) ratio of the active area of the plate and is also proportional to the ratio of the mode numbers, j/n. From the explanation above, it can be deduced that each mode induces a different out-of-plane motion in selected regions of the plate and that the amplitude of out of plane motion will be proportional to j in any given embodiment. The increasing out of plane motion that is proportional to the mode number j gives rise to a power loss that is proportional to $j^2$.

In a QCM based embodiment at least two resonant frequencies corresponding to the same values of n and m but having differing odd values of j, would be used to excite the QCM crystal. The power losses caused primarily due to viscosity would be nearly identical for at least those two resonant frequencies; however, the power losses associated with the vertical components of motion would differ in proportion to the squares of the values of j. Electrical efficiency considerations will favor n=1, m=1, and the values of j being 1 and 3 respectively for the two resonant frequency modes; however there are advantages to using additional odd values of j to obtain redundant data for minimization of measurement error. Electrical coupling of the modes of higher j order are typically diminished by 1/j, limiting the number of modes that are of practical value.

In these specifications, the term mode shall relate to a pattern of stored acoustic energy obtained by operating a crystal at, or near, a resonant frequency. In practical applications, the label antisymmetric applies only to even values of j and results from j=2 in the most preferred embodiments of the invention. In light of the present teachings, the skilled artisan will recognize that any two modes, symmetric about the center of the device or not, having different values of j will allow the practice of the disclosed invention, and further that more than two modes may be employed to obtain redundant data. In the context of mode selection, "symmetric" shall refer to a mode having in plane motion in the same direction in the regions to either side of a reference plane and "antisymmetric" shall refer to a mode having in plane motion in opposing directions in said regions.

The MCF based preferred embodiment has a split electrode and offers energy transfer between an input electrode 10 and an output electrode 11 with respect to a ground electrode 13. In the preferred embodiment, the input and output electrodes incorporate two regions collectively containing the majority of the trapped acoustic wave energy. Further, the regions associated with the two electrodes have essentially equal lateral motion essentially parallel to an axis connecting the regions across the gap therebetween for one selected mode and have essentially equal but opposing lateral motion parallel to said axis for a second selected mode. This type of motion is known as thickness shear mode of coupled resonance. An alternate design employs the so-called thickness twist mode, in which the axis of lateral motion is parallel to the gap between the electrodes. It is possible to align the electrodes and the crystal such that conditions intermediate to these two conditions will exist. The degree to which the axis of motion is perpendicular to the gap determines the degree to which the effect which enables the present invention to be exhibited.

Another preferred embodiment of a multi-mode structure employs the transverse-coupled resonator filter, commonly known as TCRF, most preferably implemented with a shear horizontal surface-guided acoustic wave. The TCRF is completely analogous to the MCF however the waves may be trapped to the transducer surface as is well known for surface acoustic wave (SAW) devices and have a periodic variation in the Z direction corresponding to the period of the interdigital transducer (IDT) employed to generate the wave. One skilled in the art will appreciate that the even and odd modes of the quasi-shear-horizontal TCRF waveguide structure are analogous to the j=1 and j=2 modes of the MCF.

Figure 5:
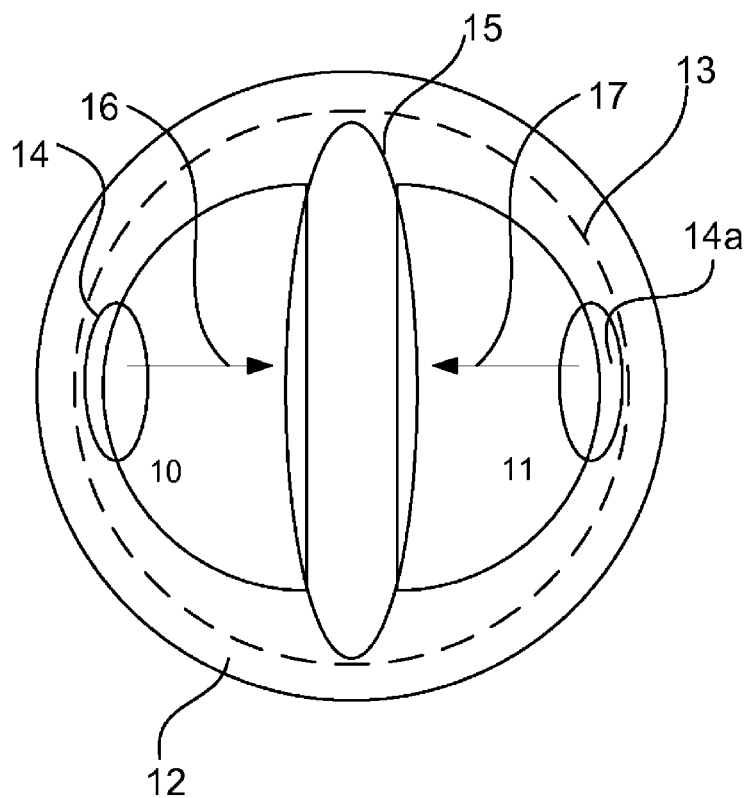
FIG. 5 depicts a top view of a preferred embodiment.
Figure 6:
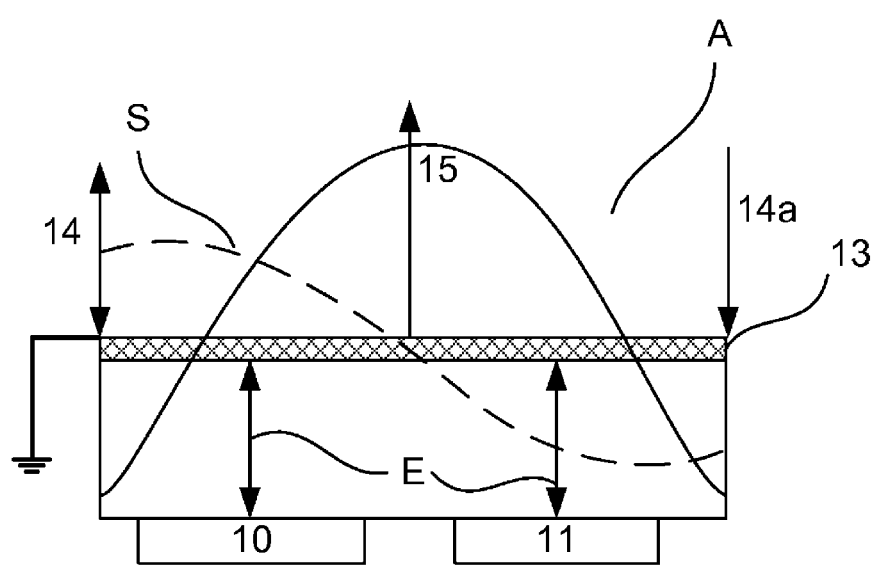
FIG. 6 depicts a cutout side view of the embodiment of FIG. 5.

FIGS. 5 and 6 depict a simple embodiment of the invention. FIG. 5 provides a top view showing a piezoelectric disc 12, having electrodes 10 and 11 deposited thereupon. Preferably, a ground electrode 13 is deposited on the opposite side of the plate; however in some embodiments it is interdigitated within the electrode or—in the case of lateral field excitation—is nonexistent. FIG. 6 provides a side view. When energy E is provided to the disc by electrode 10 and/or 11 at the natural resonant frequency, $F_1$ for which the lateral motions under electrode 10 and electrode 11 are in phase (0°), the component of the wave amplitude that lies out-of-plane, or the vertical movement, is depicted by curve S. When the energy is provided to electrode 10 and/or 11 at the natural resonant frequency, $F_2$ for which the lateral motions under electrode 10 and electrode 11 are out-of phase (180° as implied by arrows 16 and 17), the vertical movement is depicted by curve A. It is seen therefore that in the edge regions 14 and 14a vertical movement exists in both the symmetric and the anti-symmetric modes, while the vertical movement 15 above the inter-region space 4 is far larger and is induced only to modes for which j>1. The number of such regions and their exact location depend on j and only for even values of j is such a region of vertical movement located at the center of the device. The skilled in the art will recognize that excitation of the input electrode 10 at a frequency other than the exact natural resonant frequency is possible, but that substantial deviations of frequency will provide different phase relationships between the lateral motion under electrodes 10 and 11 through a superposition of the two natural modes of resonance. In light of this disclosure, the skilled in the art will further understand that the use of reproducibly and sufficiently small offset frequencies will result in reproducible factors that can be solved to obtain the desired fluid properties. Therefore the description of $F_1$ and $F_2$ shall be taken to define the preferred embodiment and not an exact limiting condition. One skilled in the art will further recognize that the resonant characteristics of the structure will vary with changes in the loading of the surface, with temperature, pressure and other environmental influences. Furthermore, while the description provides for feeding the energy to electrode 10, it is noted that this represents but one optional mode of operation, and the principle provided herein, and the invention, extends to equivalent modes of operation such as feeding energy to both electrodes 10 and 11 with respect to ground electrode 13, and the like.

The preferred embodiment utilizes a two pole piezoelectric device. The input and output resonators are coupled to each other via the substrate and are mutually coupled, i.e. the perturbation originating in the input resonator reach the output resonator, and vice versa, so as to provide the desired two pole frequency transfer function. In order to achieve such close coupling the distance between the input and output transducers could be calculated or approximated by methods specific to the particular resonator geometry and widely published in the literature. In general, the calculation involves first estimating the extent of the evanescent or fringing mechanical fields outside one resonator and in the direction of the other resonator, then evaluating the overlap of the fringing fields of one resonator with those of the other resonator, said degree of interaction representing the coupling factor between said resonators. The preferred method of calculation is to treat the structure in cross section as a multi-region, one-dimensional, waveguide with boundary conditions between said regions of continuity of mechanical amplitude and continuity of mechanical stress. Such boundary value analysis yields coupled differential equations that may be solved for the symmetric and anti-symmetric modes of the coupled structure and the associated frequencies. This method of calculating is but one of many known to the skilled in the art, and any convenient method may be used. While the foregoing disclosure employs two semi-circular geometries for manufacturing simplicity, rectangular, circular, elliptical, hyperbolic, parabolic and other resonator shapes that are equally applicable are known, and in some applications preferred.

Figure 7:
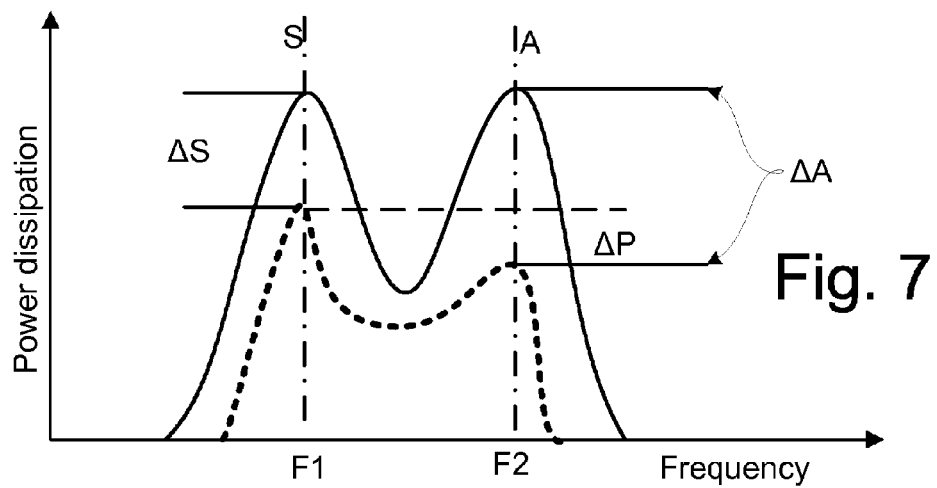
FIG. 7 depicts the difference in insertion loss between loaded and unloaded liquid modes of operation according to the preferred embodiment.

Thus, as depicted in FIG. 7, there is a difference in insertion loss between the unloaded and liquid loaded modes of operation, as measured at or near $F_1(\Delta S)$ and $F_2(\Delta A)$. The power dissipation at the lower frequency $\Delta S$ is due primarily to shear wave energy dissipation at the boundary between the device and the liquid, however the power loss at the higher frequency $\Delta A$ consists primarily of this viscous loss and an additional loss, $\Delta P$, due to compressional energy radiated into the fluid. The power dissipation is typically characterized as insertion loss for a two port device such as the MCF or the TCRF. For a single port AWD such as a QCM or a lateral field resonator, the lost energy is observed as a resistive term in the impedance versus frequency function and the resistance increases to represent a higher loss and lower quality factor resonance. Two-port insertion loss can be converted into equivalent resistance values as seen in FIG. 8, allowing a common basis of analysis.

Figure 8:
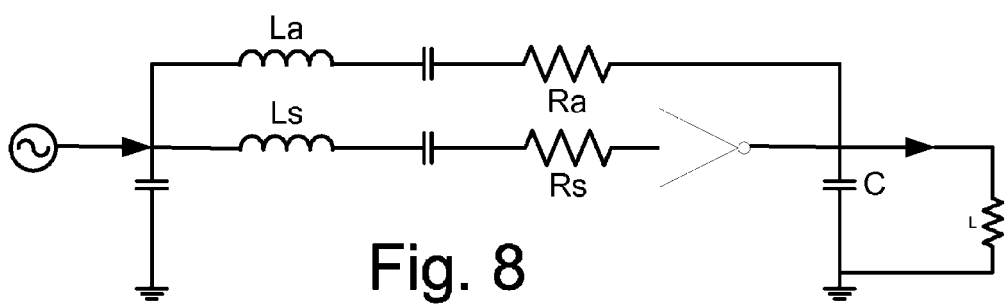
FIG. 8 depicts an equivalent circuit for a two port MMQSH resonator.

FIG. 8 describes an equivalent circuit for a two port MMQSH resonator sensor operated in accordance with the preferred embodiment. This phenomenological model provides for the physical electrode capacitances to ground of the two transducers and acoustically couples them by mechanical resonances having 0° (series resonant at $F_2$) and 180° (series resonant at $F_1$) transmission phases. The electrode capacitances represent the physical capacitance of the input electrodes and output electrodes. For the parallel plate of an MCF it is possible to express $C_o$ as $\epsilon A/t$ for a device with electrode overlap area, A, thickness, t, and dielectric constant, $\epsilon$. More complete formulae are known for interdigital transducers and for lateral field electrodes. Commonly, a capacitance ratio based on the piezoelectric coupling coefficient of the material, $k^2$, is introduced to obtain the motional capacitance of the series resonant circuits in terms of the static capacitance. Alternately, one can define an electromechanical turns ratio of an effective transformer between the acoustic and electric circuits in terms of the geometrical factors above and the piezoelectric constant, $e_{26}$, as $$\alpha = \sqrt{\frac{8e_{26}^2 A}{t}}.$$

Using this ratio it is possible to relate the motional capacitance, $C_{mot}$, at the $N^{th}$ harmonic of the resonator to the effective elastic constant of the crystal, $C_{66}$, as $$C_{mot} = \frac{\alpha^2}{C_{66}N^2\pi^2}.$$

The motional inductance, $L_m$, can be set to obtain the desired natural resonance frequency or it may be approximately related to the density of the crystal, $\rho$, and thickness, t, as $$L_{mot} = \frac{\rho t^2}{\alpha^2}.$$

Neither $C_{mot}$ or $L_{mot}$ properly account for the finite lateral dimensions or the so-called anharmonic numbers, m or j. It is therefore better to estimate $C_{mot}$ and then calculate $L_{mot}$ from a measured natural resonant frequency. In any case these parameters are only needed if one excites the device with energy at a frequency other than a natural resonance frequency such that the impedance is determined by a plurality of elements. For a device with narrow resonance widths and moderate losses the electrical properties at the resonances will be determined purely by the associated motional resistances since the natural frequencies are, by definition, the frequencies at which the inductance and capacitance cancel through series resonance in the associated transmission path. The crystal term of the motional resistance is approximately independent of mode numbers, m or j, and may be written in terms of the crystal viscosity, $\eta_{66}$, as $$R_{mot} = \frac{\eta_{66}N^2\pi^2}{\alpha^2}.$$

These parameters describe the MCF in the absence of fluid loading. For a typical device in the low MHz frequency band, $C_{mot}$ is in femtofarads, $L_{mot}$ is in millihenries, and $R_{mot}$ is in single Ohms. It is intuitively satisfying that the quality factor of the resulting series resonance is $$Q_m = \frac{C_{66}}{\omega\eta_{66}},$$

which results in the well-known frequency-Q product of crystal resonators.

The viscous effects of fluid loading have also been derived by Martin and may be modeled by an increase in the mechanical inductance and resistance. These terms may be written as $$R_F = \omega L_F = \frac{\sqrt{2\omega\eta_F\rho_F t^2}}{\alpha^2},$$

where $\eta_F$ and $\rho_F$ are the shear viscosity and mass density of the fluid, respectively.

There exists one additional term in the resistance that requires estimation, and describes the compressional wave radiation resistance. This term is roughly approximated as $$R_C(n, m, j) = \frac{\left(\frac{jt}{n\ell}\right)^2 \sqrt{c_F\rho_F}}{2\alpha^2}.$$

The dependence of this term on the mode number, j, and the ease of measurement of the resistance at one or more modes of differing values of j allow for the estimation of $(\rho_F\eta_F)^{1/2}$ and $(\rho_F c_F)^{1/2}$.

The difference between $\Delta S$ and $\Delta A$ is related to $\sqrt{c_F\rho_F}$. In particular the insertion loss can be used to estimate the resistance at the resonance associated with j=1 before and after fluid loading, in which case $\Delta S$, expressed as resistance change, yields $$\Delta R_S = K_o\sqrt{\eta_F\rho_F} + K_1\sqrt{c_F\rho_F} + \epsilon$$

and the resistance change at the resonance for which j=2, in which case $\Delta A$, expressed as resistance change, yields $$\Delta R_A = K_o\sqrt{\eta_F\rho_F} + K_2\sqrt{c_F\rho_F} + \epsilon$$

where $K_2 \sim 4K_1$, or for any other value of j, $$\Delta R_j = K_o\sqrt{\eta_F\rho_F} + K_j\sqrt{c_F\rho_F} + \epsilon$$

where $K_j \sim j^2 K_1$ for j=1, 2, 3 . . . , $K_o$ is assumed to be independent of j, and $\epsilon$ represents the sum of other losses as an error term, assumed to be zero or implicitly extracted through the remaining discussions. In real devices $K_o$ will depend slightly on mode number and an average would be used analytically.

The factor of 4 corresponds to the square of j=2. Taking the difference, expressed as resistance change, yields $\sqrt{c_F\rho_F}$ as $$\sqrt{c_F\rho_F} = \frac{\Delta R_A - \Delta R_S}{(K_2 - K_1)}$$

and $\sqrt{\eta_F\rho_F}$ as $$\sqrt{\eta_F\rho_F} = \frac{\Delta R_S - K_1\sqrt{c_F\rho_F}}{K_o}.$$

Solving this system of equations requires that one of the three variables be known or assumed, allowing a device and method of use thereof for the measurement of two fluid parameters. Note that in real devices the values of j are not exactly integers and the associated term, $K_j$, is best obtained through sensor calibration.

A note is taken that the above equations are approximate and illustrative only to a preferred embodiment and that similar equations and methods would use different coefficients. The common aspect is that the difference of losses between two modes will allow deducing information on the product of fluid density and elastic constant while the extrapolation back to zero compressional radiation will allow deducing information on the product of viscosity and density.

The skilled in the art will recognize that the method involves a linear curve fit of the loss terms to the mode number in which the slope of the fit obtains the product of fluid density and elastic constant while the extrapolation back to zero mode number will obtain information on the product of viscosity and density. It is therefore apparent that more than two modes could be measured and that a least square error fit may be advantageously used to obtain the unknown fluid property terms associated with $K_j$ instead of the direct solution above.

Figures 9, 10:
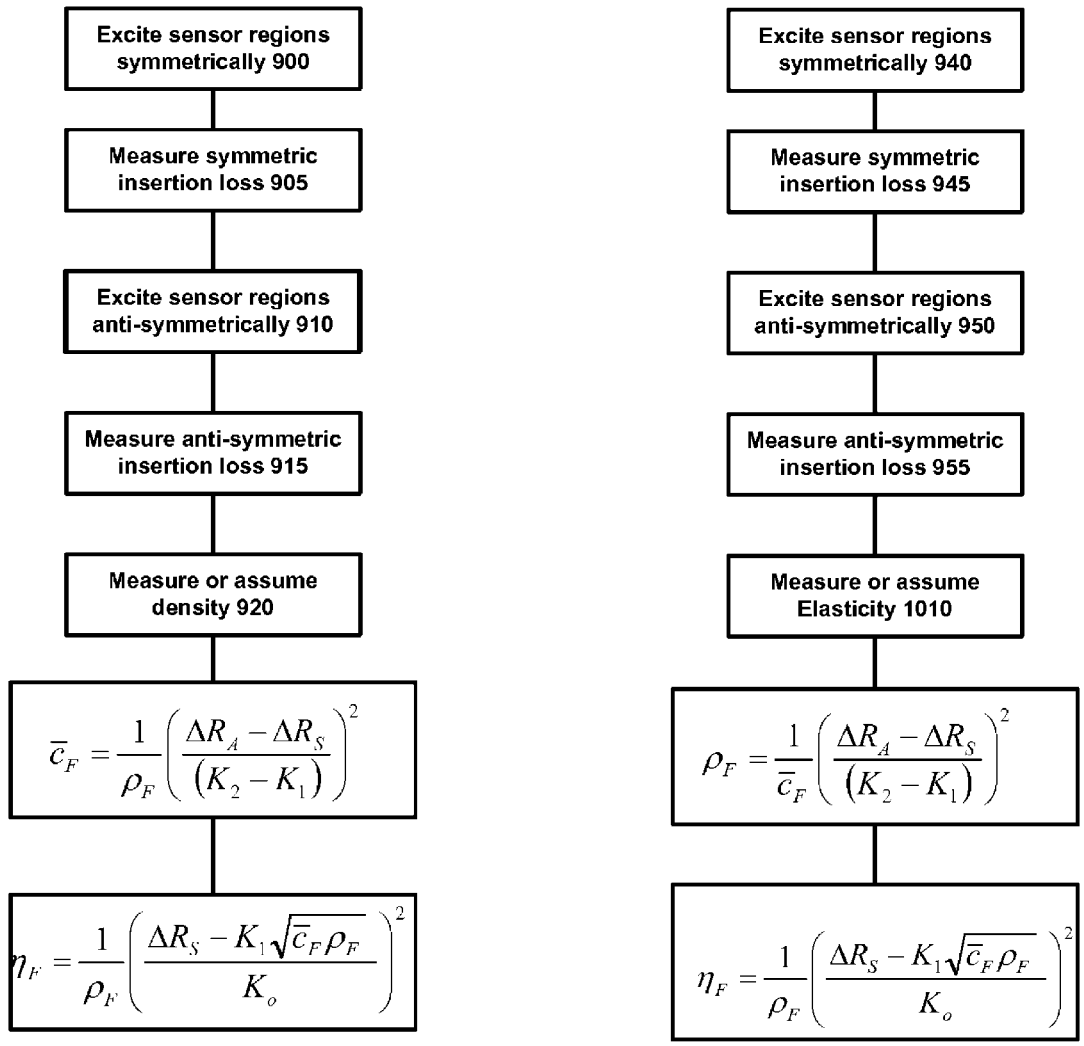
FIG. 9 is a simplified flow diagram of measuring viscosity and elastic modulus of a fluid, using a MMQSH sensor.
FIG. 10 is a simplified flow diagram of measuring density and viscosity of a fluid using a MMQSH sensor.

Therefore, a method is provided for measuring the viscosity ($\eta_F$) and elastic modulus ($c_F$) of a fluid, given a measured or an assumed density ($\rho_F$). The method is depicted in FIG. 9, and comprises providing a MMQSH resonator having a plurality of natural frequencies corresponding to a plurality of rates of variation of the wave amplitude along the X axis (mode numbers, $j_n$). Exciting the AWD with energy E at a first natural resonant frequency $F_1$, corresponding to mode number $j_1$ and having slope $K_1$, at which two different regions move in phase and then exciting the AWD with energy E at a second natural resonance frequency $F_2$, corresponding to mode number $j_2$ and having slope $K_2$, at which the two different regions move in opposite phase 900 and 910 respectively, and measuring the symmetric and anti-symmetric insertion loss 905 and 915 respectively and then calculating the change in loss from a known loss without fluid. Note that $K_1$ and $K_2$ herein represent two known slopes for a first and second value of j and are not necessarily associated with j=1 and j=2 as in the earlier example.

It is noted that in these specifications, symmetry and anti-symmetry denote the relative motion of two regions and not a specific symmetry about the geometrical center of the device. In the most preferred embodiment the symmetry of motion and symmetry of geometry are equivalent but there exist numerous alternate implementations and embodiments.

By measuring, estimating, or assuming 920 the fluid density ($\rho_F$), the elastic modulus ($c_F$) may be calculated by:

$$\bar{c}_F = \frac{1}{\rho_F}\left(\frac{\Delta R_A - \Delta R_S}{(K_2 - K_1)}\right)^2$$

and the viscosity ($\eta_F$) may be derived by $$\eta_F = \frac{1}{\rho_F}\left(\frac{\Delta R_S - K_1\sqrt{\bar{c}_F \rho_F}}{K_o}\right)^2.$$

Using a similar sensor, a method is also provided for measuring the viscosity ($\eta_F$) and the density ($\rho_F$) of a fluid, given a measured or assumed elastic modulus ($c_F$). The method is depicted in FIG. 10, and comprises providing a piezoelectric sensor having a plurality of natural frequencies corresponding to a plurality of rates of variation of the wave amplitude along the X axis corresponding to values of the mode numbers, $j_n$. Exciting the AWD with energy E at a first natural resonant frequency $F_1$ at which two different regions move in phase and then exciting the AWD with energy E at a second natural resonance frequency at which different regions move in opposite phase 940 and 950 respectively, and measuring the symmetric and anti-symmetric insertion loss 9455 and 955 respectively and then calculating the change in loss from a known loss without fluid. By measuring, estimating, or assuming 1010 the fluid elastic modulus ($c_F$), the density ($\eta_F$) may be calculated by:

$$\rho_F = \frac{1}{\bar{c}_F}\left(\frac{\Delta R_A - \Delta R_S}{(K_2 - K_1)}\right)^2$$

and the viscosity ($\eta F$) may be derived by $$\eta_F = \frac{1}{\rho_F}\left(\frac{\Delta R_S - K_1\sqrt{\bar{c}_F \rho_F}}{K_o}\right)^2.$$

Figure 11:
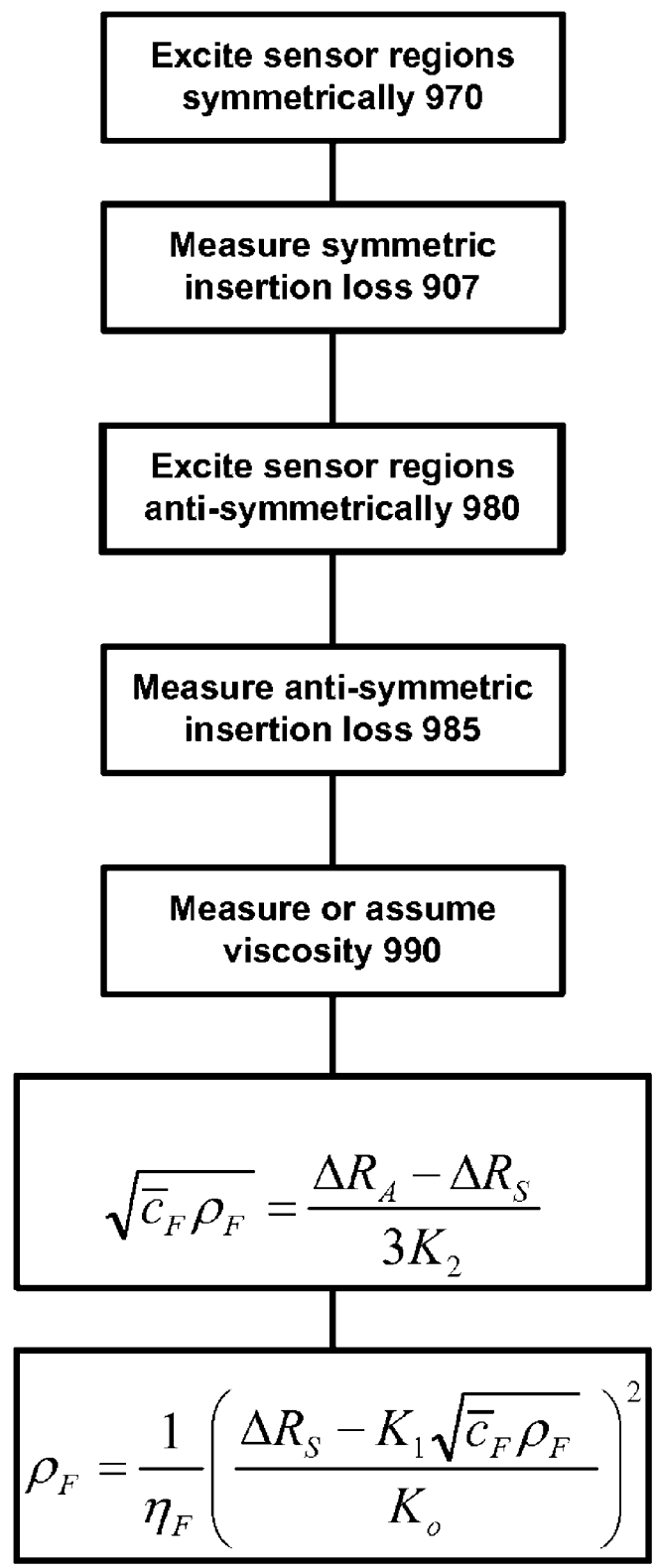
FIG. 11 is a simplified flow diagram of measuring density and elastic modulus of a fluid using a MMQSH sensor.

Further similarly, a method is also provided for measuring the density ($\eta_F$) and the elastic modulus ($c_F$) of a fluid, given a measured or assumed viscosity ($\eta_F$). The method is depicted in FIG. 11, and comprises providing a piezoelectric sensor having a plurality of natural frequencies corresponding to a plurality of rates of variation of the wave amplitude along the X axis, corresponding to the mode numbers, $j_n$. Exciting the AWD with energy E at a first natural resonant frequency $F_1$ at which two different regions move in phase and then exciting the AWD with energy E at a second natural resonance frequency at which different regions move in opposite phase 970 and 980 respectively, and measuring the symmetric and anti-symmetric insertion loss 975 and 985 respectively and then calculating the change in loss from a known loss without fluid. By measuring, estimating, or assuming 990 the fluid viscosity ($\eta_F$), an intermediate term is calculated by $$\sqrt{\bar{c}_F \rho_F} = \frac{\Delta R_A - \Delta R_S}{K_2 - K_1}$$

and the density ($\eta_F$) may be calculated as $$\rho_F = \frac{1}{\eta_F}\left(\frac{\Delta R_S - K_1\sqrt{\bar{c}_F \rho_F}}{K_o}\right)^2.$$

Figure 7B:
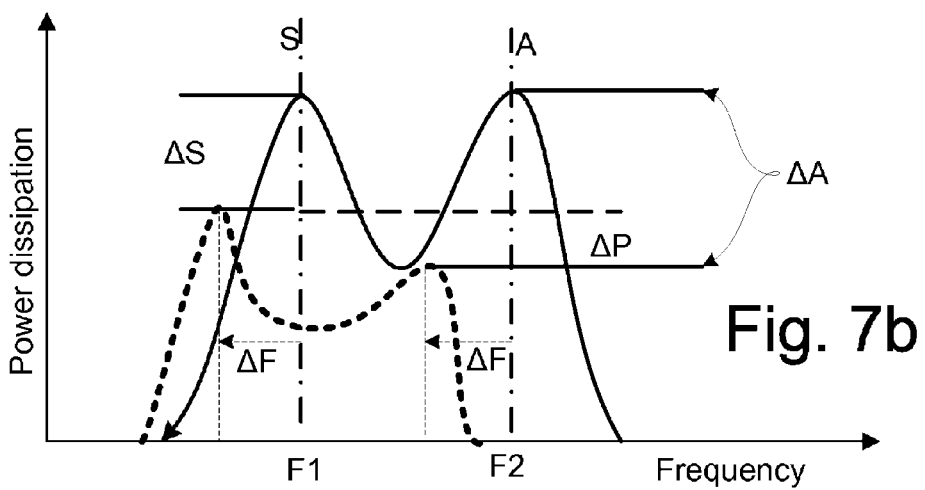
FIG. 7b illustrates the additional change in frequency which occurs due to liquid trapped in optional corrugations.

As described above, U.S. patent application Ser. No. 10/597,487 teaches measuring fluid density utilizing a corrugated surface to trap liquid over essentially the entire area of the sensing surface. Since the textured surface may be practiced with various aspects disclosed in the present application without detracting therefrom, using the teachings of the present application in combination with the '487 application is further contemplated, wherein the invention described in the '487 application is used to estimate the measured fluid density, and allow calculating the three characterizing parameters of density, viscosity and elastic modulus from the measurements obtained by a single sensor. FIG. 7b illustrates that an additional change in frequency, $\Delta F$, occurs due to the trapped liquid in the corrugations. This change is in addition to other changes that may exist due to the viscosity as are known to sufficiently skilled artisans. Knowledge of the frequency shifts provides the necessary third piece of information, allowing a measured density to be employed in the analysis of elasticity and viscosity. A consideration that needs to be accounted for when incorporating the methods of the '487 patent with the present invention are to properly select the varying frequencies, $F_n$, corresponding to the mode numbers, $j_n$, to properly account for the mass loading shifts, $\Delta F_n$, due to density of the fluid trapped in the corrugations.

While the preferred embodiment utilizes insertion loss as the measured parameter, the skilled in the art will recognize that series equivalent resistance, resonance Q, and other measurements will change similarly due to fluid loading, and may be equivalently used in the manner described for insertion loss or equivalent series resistance. Therefore, the use of parameters like insertion loss, resistance, change in Q, and other similarly effected sensor parameters should be considered equivalent, and both the claims and description extend thereto.

The properties and the magnitude of the radiated energy depend on the fluid elastic modulus, $c_F$, and fluid density, $\rho_F$, as well as the mean square amplitude of the component of motion normal to the surface, $|U_y|^2$. It is seen that the radiated energy varies as $j^2$ and that there is nominally a four to one difference in this term between $j=2$ and $j=1$ and a nine to one ratio between $j=3$ and $j=1$.

Further, the specifications and drawings depict electrical excitation through the thickness fields; however lateral field excitation is well known and is equally applicable. In fact, the scope of the invention is not limited by how the plate 1 face movement is excited, and even the use of piezoelectric material is not central to the scope of the invention. Numerous other means by which an electronic circuit may interact with acoustic waves confined in a solid material in contact with a fluid are well known. By way of example, the electromagnetic acoustic transducer (EMAT) is one such alternative as is the use of current carrying wires deposited on the substrate, interacting with a magnetic biasing field. The skilled in the art will also recognize that the invention scope extends to such methods of excitation. It becomes apparent to the skilled in the art that at least one surface of a solid material supporting waves with multiple modes resulting from lateral confinement along the axis of quasi-shear-horizontal displacement enables the primary aspects of the invention. Energy trapping can occur through mass loading of acoustic resonators even in non-piezoelectric materials. Shear waves can be excited on non-piezoelectric materials using magnetic interactions and other well-known methods. Therefore, the invention extends to using such a resonator where an added mass defines a region of trapped energy, and the region supports a plurality of laterally confined modes. The modes interact with at least one transducer, which provides electrical impedance related to energy loss in the laterally-confined trapped energy resonator.

In fact, certain embodiments of the invention need not employ a traditional bulk acoustic wave resonator, and may be practiced using planar resonators based on acoustic plate modes, shear horizontal surface acoustic waves and the like, provided conditions of the coupled wave can be obtained that satisfy the requirements described for the bulk acoustic wave resonator described above, namely a first and second mode having differing lateral amplitude profiles along an axis defined by the polarization of the shear surface amplitudes. For example, placing the waveguiding structures of two such surface generated acoustic wave devices in close proximity creates a transversely-coupled resonator filter. The directions of motion are the same in both waveguides for one coupled mode and are anti-parallel for another.

Figure 13:
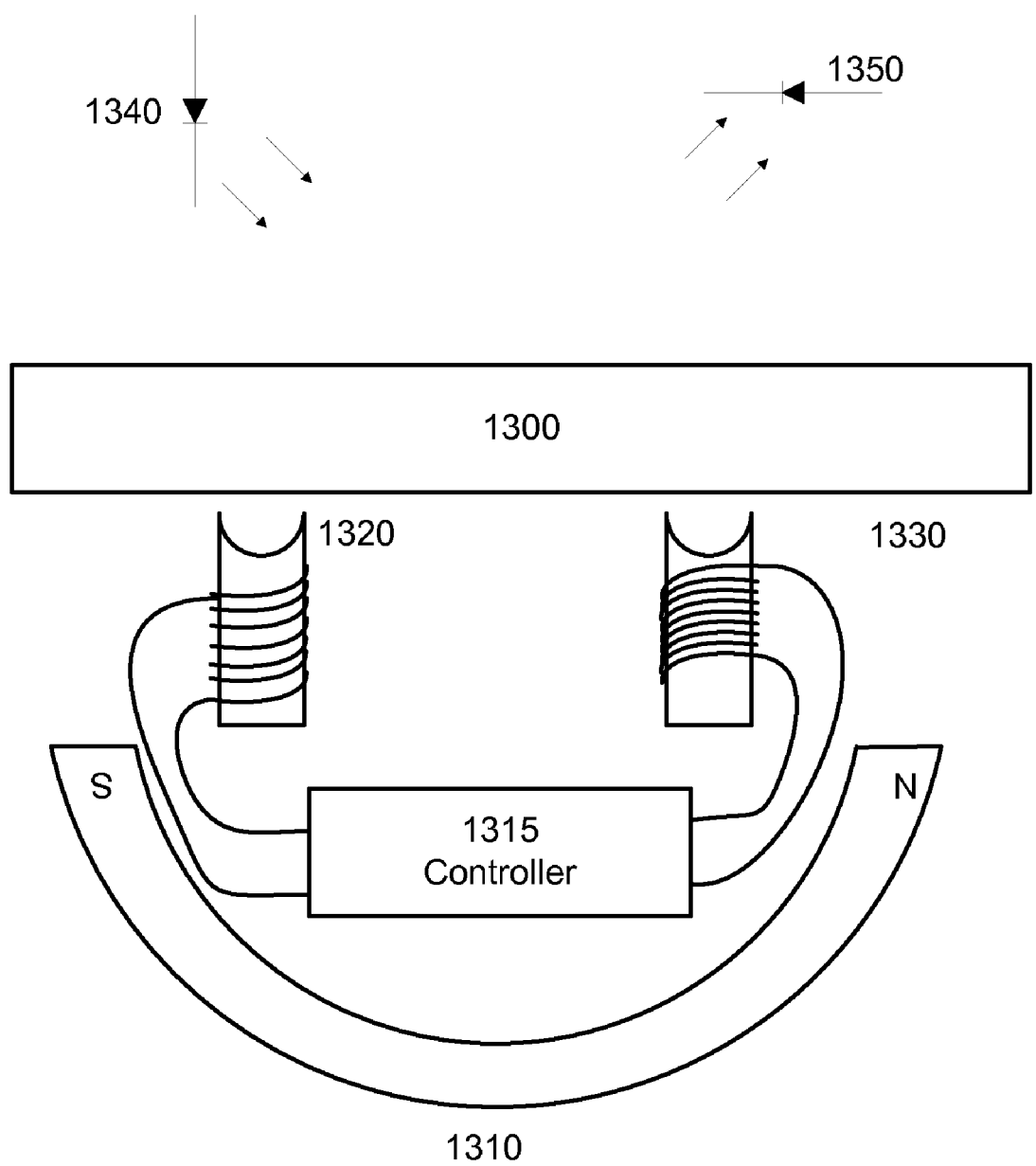
FIG. 13 depicts a simplified schematic depiction of a system utilizing a non-piezoelectric resonator.

Thus by way of example, in yet another optional embodiment, FIG. 13 depicts a simple schematic depiction of a system operated utilizing such metal resonator 1300 and a magnetic biasing field 1310. A controller 1315, capable of providing current at varying frequencies, and/or power levels, supplies oscillating energy to electromagnets exciters 1320 and 1330. A resonator, such as a metal disk 1300, is at least partially disposed within the biasing magnetic field and the oscillating magnetic field of exciters 1320 and 1330. Resonator 1300 has an energy trapping structure for lateral confinement. Eddy currents caused by the oscillating field create time-harmonic force fields within the metal disk. With judicious polarization of the biasing magnetic field and orientation of the conductors of the electromagnets, these forces give rise to quasi-shear-horizontal acoustic waves with a number of natural frequencies corresponding to the various modes allowed by the lateral confinement. The resistance of the metal resonator to motion, due to the viscosity, density, and elasticity of the adjacent fluid, is observed as a change in transfer loss between the coils or a change in resistive losses within a single coil. This occurs due to reciprocity of the coupling mechanism between the coils and the resonator. Alternately a detecting mechanism such as optical transmitter 1340 and receiver 1350 track the movement of the separation area formed between the regions, and thus provide information, that is then utilized in calculating the desired fluid parameters. While it is noted that it is not necessary to have the regions excited in one mode, or the separation zone therebetween, be the same as those of the second mode, the preferred embodiment calls for those regions to be in registration, so as to simplify calculations and minimize the effects of non-uniformity in the resonator. It is imperative to understand that FIG. 13 is provided merely as a simplified, non-limiting example, and that other embodiments are within the scope of the invention and within the scope of the artisan with ordinary skill in the art. No effort is made to depict a practical alignment of the biasing and driving fields in the figure.

Figure 12:
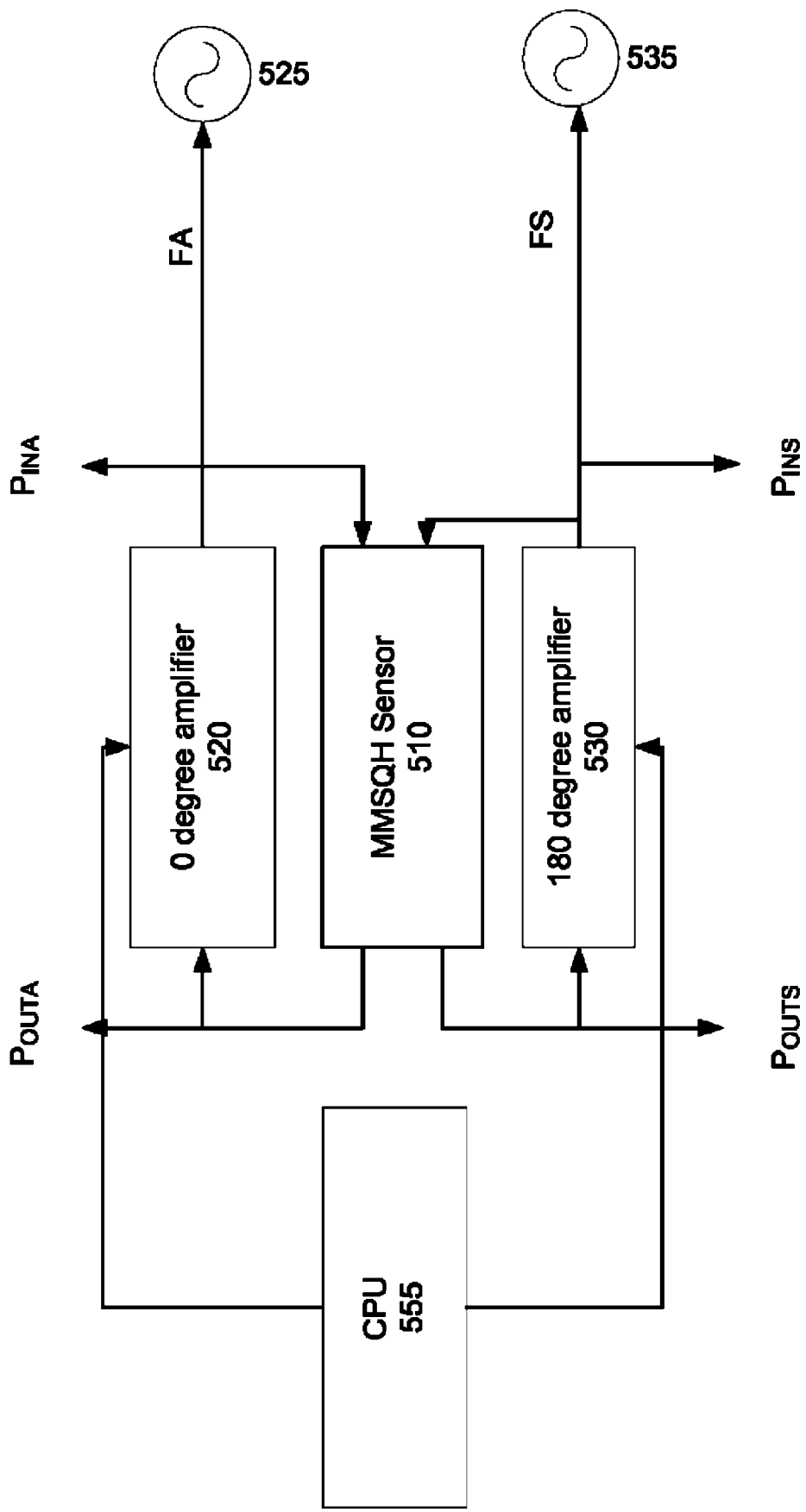
FIG. 12 is a simplified block diagram of a system utilizing an MMSQH for measurement of fluid parameters.

The preferred simplest support circuit for deriving the fluid parameters contemplated in these specifications uses a subset of the block diagram of FIG. 12. The resonant frequency, $F_A$, is tracked by employing the sensor element, 510, as the feedback element of a zero-phase amplifier, 520. At the zero-phase resonance, $F_A$, oscillation will occur in this loop if the amplifier gain exceeds the sensor element loss and the net phase of the loop is substantially zero or a multiple of 360°. The frequency is measured by frequency sensing apparatus such as a frequency counter, 525.

In order to measure the viscosity as well as the density, the resonant frequency $F_S$ is tracked by employing the sensor element 510 as the feedback element of a 180° amplifier 530, and a frequency sensing circuitry such as frequency counter 535. While not shown, the skilled in the art will realize that different circuitry is equivalently applicable for sensing the common mode frequency shift, such as frequency mixing, and the like. Using the methods taught in US patent application publication 2007-0144240-A1, in combination with the formulae provided herein, any two parameters of the group consisting of viscosity, density, and elastic modulus, may be calculated if the third parameter is known or assumed, for example by using the sum and difference of power levels $P_{INA}$ and $P_{OUTA}$, or $P_{INS}$ and $P_{OUTS}$ respectively, and utilizing the above provided formulae.

Thus, yet another aspect of the invention extends to a system comprising a piezoelectric MMQSH resonator, having an input and an output, circuitry to excite the MMQSH resonator so as to cause the MMQSH resonator to resonate in at least two modes, and circuitry to measure at least one parameter of the energy inputted into the MMQSH resonator or outputted therefrom. The two modes are selected to cause tangential motion with differing polarity at various regions of the surface of the MMQSH resonator. The parameters measured may be, by way of example, insertion loss, frequency shift, phase shift, amplitude, and the like.

It is noted that the teachings of U.S. Pat. No. 7,181,957 and U.S. Pat. No. 7,219,537, may be advantageously used with the present in invention and both patents are incorporated herein by reference.

The most preferred embodiments have separate transducers for the input and output electrical ports; however it is equally permissible to input and output the electrical signals via a common port and such devices shall still be deemed to have an input and an output. It may also be desirable to electrically generate a signal and to optically or mechanically monitor its amplitude to detect changes in power dissipation. These variations are all within the scope of measuring the plurality of power losses of a plurality of multiple modes of a quasi-shear-horizontal AWD.

The preferred embodiment employs a plurality of modes associated with a single acoustic wave type and more preferably with a single value of the mode numbers, n and m, most preferably using the quasi-shear-horizontal wave type for n=m=1. Higher order modes in n and m are applicable. The use of two different polarizations of shear wave (e.g. X and Z polarized) in a crystal cut that electrically supports the excitation of both wave types is also feasible. For example SC-quartz and similar doubly rotated cuts allow the excitation of two shear modes. One skilled in the art realizes that these two modes can be adapted for the purpose of exciting multiple modes with differing loss contributions due to compressional wave generation, thereby accomplishing the fundamental teachings of the invention.

It will be appreciated that the invention is not limited to what has been described herein above merely by way of example. While there have been described what are at present considered to be the preferred embodiments of this invention, it will be obvious to those skilled in the art that various other embodiments, changes, and modifications may be made therein without departing from the spirit or scope of this invention and that it is, therefore, aimed to cover all such changes and modifications as fall within the true spirit and scope of the invention, for which letters patent is applied.

I claim:

1. A method of measuring at least two fluid properties selected from density, viscosity, and elastic modulus, when the third of said fluid properties is known or assumed, the method comprising the steps of:
    providing a Multi Mode Quasi Shear Horizontal Resonator (MMQSHR) having an energy input, and a measuring surface for contacting said fluid, said measuring surface having at least a first region and a second region, and a separation area defined therebetween;
    feeding said MMQSHR with excitation energy via said input, at a first frequency and then at a second frequencies selected to excite a first and a second acoustic modes respectively, each of said acoustic modes causing a component of horizontal shear wave motion in said surface, wherein excitation in said first frequency further causing said regions to move in phase relative to each other; and wherein excitation in said second frequency causes said two regions to move out-of-phase relative to each other, inducing a vertical displacement in said separation area;
    measuring energy related parameters at said first mode and second mode;
    calculating two of said fluid properties utilizing said energy related parameters and information relating to said third fluid property.

2. A method as claimed in claim 1 wherein said energy related parameters are selected from a list consisting of insertion loss, frequency shift, phase shift, amplitude, current change, equivalent series resistance, or a combination thereof.

3. A method as claimed in claim 1, wherein said MMQSHR comprises a piezoelectric crystal, and wherein said input comprises an input transducer.

4. A method as claimed in claim 1, wherein said step of calculating occurs separately for each of said calculated fluid properties.

5. A method as claimed in claim 3, further comprising an output transducer, wherein said input transducer and said output transducer are referenced to an opposing ground electrode.

6. A method as claimed in claim 3, wherein said MMQSHR sensor employs a structure selected from a group consisting of bulk acoustic wave resonator, planar resonator, and shear horizontal surface acoustic wave resonator.

7. A method according to claim 1, wherein said elastic modulus is one of said two fluid properties to be measured, and wherein said elastic modulus is calculated according to the formula $$\bar{c}_F = \frac{1}{\rho_F}\left(\frac{\Delta R_A - \Delta R_S}{(K_2 - K_1)}\right)^2.$$

wherein
$\bar{c}_F$ being the elastic modulus of said fluid;
$\rho_F$ being the density of said fluid;
$\Delta R_A$ being the difference between the equivalent resistance of said MMQSHR when operated in antisymmetric mode in an unloaded state, and the equivalent resistance of said MMQSHR when operated in antisymmetric mode while being loaded by said fluid;
$\Delta R_S$ the difference between the equivalent resistance of said MMQSHR when operated in symmetric mode in an unloaded state, and the equivalent resistance of said MMQSHR when operated in symmetric mode while being loaded by said fluid; and
K1 and K2 being two calibration parameters.

8. A method according to claim 1, wherein said viscosity is one of said two fluid properties being measured, and wherein said viscosity is calculated according to the formula $$\eta_F = \frac{1}{\rho_F}\left(\frac{\Delta R_S - K_1\sqrt{\bar{c}_F \rho_F}}{K_o}\right)^2$$

wherein
$\eta_F$ being the viscosity of said fluid;
$\rho_F$ being the density of said fluid;
$\bar{c}_F$ being the elastic modulus of said fluid;
$\Delta R_S$ the difference between the equivalent resistance of said MMQSHR when operated in symmetric mode in an unloaded state, and the equivalent resistance of said MMQSHR when operated in symmetric mode while being loaded by said fluid; and,
K1 and K2 being two calibration parameters.

9. A method according to claim 1, wherein said density is one of the two fluid properties being measured, and wherein said density is calculated according to one of the formulae $$\rho_F = \frac{1}{\bar{c}_F}\left(\frac{\Delta R_A - \Delta R_S}{(K_2 - K_1)}\right)^2 \text{ or } \rho_F = \frac{1}{\eta_F}\left(\frac{\Delta R_S - K_1\sqrt{\bar{c}_F \rho_F}}{K_o}\right)^2$$

wherein
$\rho_F$ being the density of said fluid;
$\eta_F$ being the viscosity of said fluid;
$\Delta R_A$ being the difference between the equivalent resistance of said MMQSHR when operated in antisymmetric mode in an unloaded state, and the equivalent resistance of said MMQSHR when operated in antisymmetric mode while being loaded by said fluid;

$\Delta R_S$ the difference between the equivalent resistance of said MMQSHR when operated in symmetric mode in an unloaded state, and the equivalent resistance of said MMQSHR when operated in symmetric mode while being loaded by said fluid; and, K0, K1 and K2 being three calibration parameters.

10. A method as claimed in claim 1, wherein said step of feeding comprises providing excitation energy in combination with additional frequencies, so as to cause said surface to resonate at more frequencies than said first and second frequencies.

11. A method as claimed in claim 3, wherein said piezoelectric material is cut from a crystal so as to allow a plurality of shear modes responsive to said excitation.

12. A method as claimed in claim 1, wherein said MMQSHR comprises an electrically conductive material, and wherein said excitation energy is electromagnetic.

13. A method as claimed in claim 1, wherein said step of feeding comprises providing excitation energy in combination of differing power levels at the at least two frequencies, so as to cause said surface to impart various shear rates to the fluid at each of said frequencies, allowing the measurements to be made at varying shear rate.

14. A system for measuring at least two fluid properties selected from density, viscosity, and elastic modulus, when the third of said fluid properties is known or assumed, the system comprising:

A Multi-Mode Quasi Shear Horizontal (MMQSHR) resonator having a measuring surface for contacting said fluid;

an energy input port and an energy output port;

at least a first region and a second region, and a separation area defined therebetween;

excitation circuitry coupled at least to said energy input port, and constructed to impart two acoustic modes of resonant motion to said surface;

wherein said two acoustic modes are selected to cause differing amplitudes of motion normal to said surface, when excited at the resonant frequency of said different acoustic modes;

measurement circuitry constructed to measure at least one parameter of the energy inputted into the MMQSHR resonator or outputted therefrom; and, parameter calculating processor coupled to said measurement circuitry, and constructed to calculate at least said two fluid properties when said third fluid property is known or assumed.

15. A system as claimed in claim 14, wherein said energy input port, is coupled to electrical energy source, and further comprising optical or mechanical monitor to monitor displacement of said separation area, said monitor being coupled to said measurement circuitry.

16. A system as claimed in claim 14, wherein said parameter calculating processor comprises a calculator or a computer.

17. A system as claimed in claim 14, wherein said MMQSHR comprises a piezoelectric monolithic crystal filter.

18. A system as claimed in claim 14, wherein said MMQSH comprises a piezoelectric transverse coupled resonator filter.

19. A system as claimed in claim 14, wherein said MMQSH comprises and electromagnetic acoustic transducer.

* * * * *